United States Patent [19]

Leproux et al.

[11] Patent Number: 5,756,317
[45] Date of Patent: May 26, 1998

[54] PRODUCTION OF HETEROPLYSACCHARIDE BIOPOLYMERS WITH XANTHOMONAS IN OIL-IN-WATER EMULSION

[75] Inventors: Veronique Leproux, Boulogne; Michel Peignier, L'Arbresle; Patrick Cros, Melle; Jeanine Beucherie, Massy; Yves Kennel, Melle, all of France

[73] Assignee: Rhone-Poulenc Specialities Chimiques, Courbevoie, France

[21] Appl. No.: 641,618

[22] Filed: Jan. 16, 1991

Related U.S. Application Data

[63] Continuation of Ser. No. 203,993, Jun. 8, 1988, abandoned, which is a continuation of Ser. No. 812,505, Dec. 23, 1985, abandoned.

[51] Int. Cl.$^6$ ...................................................... C12P 19/04
[52] U.S. Cl. ........................ 435/104; 435/104; 435/248; 435/249; 435/910; 435/244
[58] Field of Search ................................. 435/101, 244, 435/104, 248, 249, 822, 830, 847, 831, 910

[56] References Cited

U.S. PATENT DOCUMENTS

| | | |
|---|---|---|
| 3,997,398 | 12/1976 | Zajic ........................................ 435/101 |
| 4,352,882 | 10/1982 | Maury ...................................... 435/101 |

FOREIGN PATENT DOCUMENTS

| | | | |
|---|---|---|---|
| 0098473 | 1/1984 | European Pat. Off. ............... | 435/101 |
| 1174322 | 12/1969 | Japan ..................................... | 435/101 |
| 1174322 | 12/1969 | United Kingdom . | |

OTHER PUBLICATIONS

Rehm et al, "*Biotechnology*", vol. 3, pp. 43–50, 62–64 1983.

Ullmanns Encyklopadie der Technischen Chemie, vol. 10, 1975, pp. 449–470.

Kue Hig et al., *Biotech. and Bioeng.*, vol. XIV pp. 379–390 (1972).

Kanamaru et al, *Agr. Biol. Chem.*, vol. 33, pp. 1521–1522, 1969.

*Primary Examiner*—Irene Marx
*Attorney, Agent, or Firm*—Burns, Doane, Swecker & Mathis, L.L.P.

[57] ABSTRACT

Heteropolysaccharide biopolymers well adopted as thickening agents are improvedly produced by microbially fermenting a carbohydrate nutrient medium, said nutrient medium comprising an oil-in-water emulsion of a discontinuous oily phase dispersed within a continuous aqueous phase.

9 Claims, No Drawings

PRODUCTION OF HETEROPLYSACCHARIDE BIOPOLYMERS WITH XANTHOMONAS IN OIL-IN-WATER EMULSION

This application is a continuation, of application Ser. No. 203,993 now abandoned, filed Jun. 8, 1988 which is a continuation of now abandoned application Ser. No. 812,505, filed Dec. 23, 1985.

BACKGROUND OF THE INVENTION

1. Field of the Invention

The present invention relates to the production of polysaccharides by microbial fermentation of carbohydrates, and, more especially, to such production carried out in an oil-in-water emulsion fermentation medium.

2. Description of the Prior Art

Heteropolysaccharides or biopolymers obtained by fermentation of a carbohydrate utilizing bacteria of the genus Xanthomonas or Arthrobacter, fungi of the genus Sclerotium, and other microorganisms of like type, are useful for a wide variety of industrial applications by virtue of their thickening and viscosity increasing properties.

The production of xanthan gum by aerobic fermentation in aqueous media has been described in numerous patents. See, for example, U.S. Pat. Nos. 3,000,790, 3,020,206, 3,391,060, 3,433,708, 4,119,546, 4,154,654, 4,296,203, 4,377,637 and French Patent No. 2,414,555.

At the onset of production, the fermentation medium may contain approximately 15 to 50 g/liter of polysaccharide. Industrially, it is very difficult to exceed a concentration of 30 to 35 g/liter without the need for special measures. In effect, the increase in the viscosity of the reaction medium at the rate of the formation of the polysaccharide slows the transfer of oxygen and reduces fermentation. Even if the reactors are equipped with powerful stirring means, which are costly in view of their energy consumption, it is very difficult to insure adequate aeration and agitation of the reaction mass to permit an increase in the polymer concentration.

In order to increase the gum concentration, it has recently been proposed to carry out the fermentation in the form of an emulsion or dispersion of the aqueous nutrient medium in an oil, such as to reduce the viscosity of the wort and facilitate the transfer of oxygen. Compare published European Applications Nos. 00/58,354, 00/74,775 and 00/98,473.

However, it would appear to be preferable to effect a first stage of microorganism growth in an essentially aqueous nutrient medium prior to the introduction of the oil and the establishment of the water-in-oil emulsion. Once the water-in-oil emulsion is formed, it becomes difficult to regulate the pH of the dispersed aqueous phase and the formation of acid by-products presents the risk of inhibiting the growth of the microorganism. It is certainly possible to conduct the operation in a buffered medium, but the presence of the buffer may be harmful to the quality of the final product. Furthermore, stabilized water-in-oil emulsions are very difficult to dilute, which is disadvantageous in light of the need for the direct application of these emulsions, for example, in the exploitation of subterranean well formations/petroleum deposits.

SUMMARY OF THE INVENTION

Accordingly, a major object of the present invention is the provision of an improved fermentation process for the production of heteropolysaccharides, and one specifically designed to more readily effect the growth of microorganisms within an emulsified fermentation medium.

This invention also relates to the preparation of stable biopolymer emulsions containing up to about 60% of biopolymer.

Briefly, the present invention features the production of polysaccharides by microbial fermentation of an aqueous nutrient medium, and wherein an oil is dispersed in the aqueous medium in a manner such that an oil-in-water emulsion is formed, the fermentation being carried out therein.

DETAILED DESCRIPTION OF THE INVENTION

More particularly according to the present invention, the continuous aqueous phase may comprise any of the aqueous fermentation media well known to this art, and described, for example, in U. S. Pat. Nos. 3,391,060 and 3,433,708, and in French Patent No. 2,414,555. The "conventional" fermentation medium contains a carbohydrate source that may be a sugar or another carbohydrate, an organic and/or inorganic source of nitrogen, together with trace elements, and, if necessary, growth factors. The sugar concentration, such as glucose or saccharose, may range from 10 to 100 g/liter and may even attain a value of 150 to 200 g/liter.

The microorganism employed as the agent of fermentation may be selected from among those bacteria known to ferment carbohydrates, such as described in Bergey's, *Manual Of Determinative Bacteriology* (8th edition, 1974, Williams and Wilkins Co., Baltimore). Suitable for this purpose are, for example, *Xanthomonas begoniae*, *Xanthomonas campestris*, *Xanthomonas carotae*, *Xanthomonas hedera*, *Xanthomonas incanae*, *Xanthomonas malvacearum*, *Xanthomonas papaveri cola*, *Xanthomonas phaseoli*, *Xanthomonas pisi*, *Xanthomonas vasculorum*, *Xanthomonas vericatoria*, *Xanthomonas vitians*, *Xanthomonas pelargonii*; the bacteria of the genus Arthrobacter, and more particularly the species *Arthrobacter stabilis* and *Arthrobacter viscosus*; of the genus Erwinia; of the genus Azotobacter, and more particularly the species *Azotobacter indicus*; of the genus Agrobacterium, and more particularly the species *Agrobacteriam radiobacter, Agrobacterium rhizoqenes* and *Agrobacterium tumefaciens*. Fungi belonging to the genus Sclerotium may also be used.

Among these microorganisms, *Xanthomonas campestris* is preferably used.

With respect to the oil phase, any mineral or vegetable oil immiscible with water may be employed, for example, the isoparaffins, deodorized kerosene, hydrocarbons having a high boiling point, preferably higher than 150°–200° C., rapeseed oil, soybean oil, corn oil, sunflower oil, peanut oil, and the like. It is desirable that the proportion of the oily phase constitute less than 30% of the total fermentation medium, preferably 1 to 18% thereof, and even more preferably 3 to 16%.

The dispersion and stabilization of the oily phase in the aqueous phase are favorably influenced by the presence of surface active agents, preferably nonionic surfactants, the HLB value of which is preferably less than 11, and even more preferably ranges from 6 to 11, with this value being attained by use of a single surfactant or mixture thereof. The selection and the amount of the surfactant necessary to obtain a continuous aqueous phase can readily be determined by those skilled in this art as a function of the particular oil and its concentration in the medium.

Exemplary of the nonionic surface active agents, generally compounds obtained by the condensation of an alkylene oxide with an aliphatic or alkyl-aromatic organic compound may be utilized. Representative surfactants which do not inhibit the growth of microorganisms are the polyoxyethylene alkylphenols, polyoxyethylene alcohols, polyoxyethylene fatty acids, polyoxyethylene triglycerides, polyoxyethylene esters of sorbitan and fatty acids.

All of the surface active agents may be used either alone or as an admixture thereof. All or a portion of the surfactant or surfactants may be introduced, depending upon their affinity, into either the oily phase or the continuous aqueous phase.

To carry out the process of the invention, it is advisable to separately sterilize the oil phase and the aqueous phase. After sterilization and cooling, the oil phase may be mixed into the aqueous phase contained in the fermentation tank or else each of the phases may be continuously introduced into the fermentation vessel under agitation. A stable emulsion is immediately formed. Seeding and fermentation are then carried out in a conventional manner, with aeration and agitation. Over the course of the fermentation the pH may be maintained at its optimum value by injection therein of an alkaline or ammoniacal solution. It is also possible to periodically or continuously make additions of the medium necessary for growth.

After fermentation and depending upon the application intended, the emulsion may be used as is, or the aqueous phase may be separated from the oil phase by destabilization in a manner known, per se, and the wort may be used in the raw or crude state, or else the polysaccharide may be precipitated, for example, by the addition of a lower alcohol such as isopropanol, either with or without the aid of a mineral salt. The precipitated polysaccharide is separated, washed clean of the oil adsorbed on the fibers thereof, and then dried and optionally ground. A ready-to-use powder is obtained in this fashion.

In one particular embodiment of the process of the invention, the emulsion obtained upon completion of the fermentation process is concentrated to eliminate the water until an emulsion is produced containing 8 to 60% by weight, and preferably 15 to 60% by weight, of polysaccharides with respect to the weight of the product emulsion. In this embodiment of the invention, the amount of oil used for the fermentation must be calculated as a function of the dry solids content upon completion of the fermentation. It is preferable that the amount of oil in the final emulsion does not exceed 45% by weight of the total medium.

The water may be eliminated, for example, by evaporation or distillation, optionally under partial pressure. It is possible to eliminate a portion of the oily phase in at mixture with water, whether or not azeotropic. Ultrafiltration may also be carried out using conventional methods and equipment, with the obvious condition of selecting a porous hydrophilic membrane having pores that are sufficiently small to prevent the passage of the biopolymer through the membrane.

Ultrafiltration assures the preservation of emulsions having a continuous aqueous phase. Concentration by ultrafiltration has the further advantage of maintaining the inorganic salt content of the aqueous phase at values close to those existing in the initial wort, regardless of the polymer content.

In another embodiment of the invention, the emulsions may be initially concentrated by ultrafiltration and then by a different operation, for example, evaporation or distillation.

Without departing from the scope of the invention, bactericides, enzymes, or other additives intended for a particular application, may be added to the emulsions obtained, provided that said additives do not adversely affect the stability of the emulsion.

The advantage of the subject process vis-a-vis the inverse emulsion system are as follows:

(1) The possibility of effecting the growth of microorganisms in an emulsified medium at a normal reaction rate—the growth of the microorganisms is not disturbed by the emulsion;

(2) Energy savings during the growth phase, as the power required to agitate the fermentation medium is lower;

(3) The possibility of easily regulating the pH of the aqueous phase; and (4) The possibility of concentrating the emulsions without inversion of the phases and without precipitation of the polysaccharide.

The oil-in-water emulsions obtained according to the process of the invention may be used in any application requiring viscosified aqueous liquids, such as the building, paint, cosmetic, plant protection, petroleum, etc., industries. They have the advantage that they may be used directly for the preparation of dilute aqueous solutions without having to be subjected to phase inversion. They disperse very well in water, their rate and degree of dissolution being at least equal to that of the initial wort. They remain pumpable and stable over a very broad range of concentration. Their viscosity is substantially less than that of an aqueous solution containing an equivalent amount of biopolymer, such that it is possible to provide pourable or pumpable emulsions having high polysaccharide concentrations in the aqueous phase.

In view of these advantages the emulsions of the invention are particularly appropriate for use in the petroleum field and for the formulation of aqueous liquids intended for the assisted recovery of petroleum.

In order to further illustrate the present invention and the advantages thereof, the following specific examples are given, it being understood that same are intended only as illustrative and in nowise limitative.

In said examples to follow, a general procedure was utilized, wherein:

(i) The aqueous nutrient medium was charged into the fermentation vessel and sterilized, (ii) The oil, optionally containing the surfactant or surfactants, was sterilized and poured, under agitation, into the aqueous solution contained in the fermentation vessel at room temperature, and (iii) The medium was seeded with a preculture of *Xanthomonas campestris* on a MY saccharose nutrient solution at 10 g/l.

EXAMPLE 1

In a 20 liter fermentation tank, 14 liters of a sterile oil/water emulsion containing 6.25% by volume of the oily phase and 93.75% of the aqueous phase, were seeded with 210 g of the preculture.

| Composition of the aqueous phase: | |
| --- | --- |
| (i) Dextrose: | 61 g/l |
| (ii) Yeast extract: | 7 g/l |
| (iii) Na₂HPO₂: | 2.35 g/l |
| (iv) (NH₄)₂PO₄: | 2.2 g/l |
| (v) MgSO₄.7H₂O: | 0.35 g/l |

| Composition of the oil phase: | |
| --- | --- |
| (i) Dearomatized aliphatic hydrocarbon (Exsol D 100 marketed by Esso Chimie) | 70% by weight |
| (ii) Ethoxylnonylphenol (67/33 mixture of Cemulsol NP4 and Cemulsol NP 17 - trademarks of SFOS Company) HLB value: 11 | 30% by weight |

| Fermentation conditions: | |
| --- | --- |
| Temperature: | 28° C. |
| pH controlled at 7 by the addition of sodium hydroxide | |
| Agitation: | 400 rpm |
| Aeration from | |
| 0 to 17 hours: | 0.24 VVM |
| 17 to 23 hours: | 0.48 VVM |
| 23 to 90 hours: | 0.98 VVM |
| Fermentation until all of the sugar is depleted | |
| Duration: | 90 hours |

The growth of the microorganism population and the resistivity of the medium over time are reported in Table I which follows.

The amount of active material obtained was 425 g (30.3 g/kg), representing a yield with respect to sugar of 56%.

The viscosity of the emulsion upon completion of fermentation was 8.1 Pa·s (Brookfield viscosity 20° C.-No. 4 needle-30 t/min).

EXAMPLE 2

The procedure of Example 1 was repeated, using an initial fermentation medium composed of 29% by volume of Exsol D 100 hydrocarbons and 71% of the aqueous phase having the following composition:

(i) Dextrose: 64 g/l (ii) Yeast extract: 9.24 g/l (iii) Na₂HPO₄: 3.08 g/l (iv) (NH₄)₂PO₄: 3.08 g/l (v) MgSO₄·7H₂O: 0.35 g/l No surfactant was added.

The operating conditions were identical to those of Example 1, except for the aeration which was constant at 0.98 VVM. Fermentation was for 85 hours, at which stage no more sugar was present.

The growth of the microorganism population and the resistivity of the fermentation medium are also reported in Table I.

330 g of active material were obtained, representating a yield of 51.3% with respect to the sugar. The vicosity of the final emulsion was 10.2 Pa·s (same conditions as in Example 1).

EXAMPLE 3

The initial oil/water emulsion was formed from 14.125 liters of the aqueous phase and 0.875 liters of the oily phase.

Composition of the aqueous phase (i) Saccharose: 85 g/l (ii) Soluble corn extract: 25.5 g/l (iii) MgSO₄·7H₂O: 0.28 g/l The oily phase contained 70% by weight of rapeseed oil and 30% ethoxynonylphenols (CEMUSOL NP4).

HLB value: 9

The medium was seeded as in Example 1.

Fermentation conditions

Temperature: 28° C.

pH controlled at 7 by the addition of sodium hydroxide

Agitation from 0 to 17 hours: 390 rpm 17 to 24 hours: 500 rpm 24 to 84 hours: 600 rpm Aeration from 0 to 17 hours: 0.92 VVM 17 to 84 hours: 1.4 VVM Average power dissipated: 6.09 KW/m³

After 84 hours, 51 g xanthan gum per kg of the medium had been produced. Yield/saccharose consumed: 64%.

The consistency K (by Ostwald's law) of the medium was 37 Pa·s and the pseudoplasticity index n was 0.195.

By comparison, an aqueous wort containing 48.5 g/kg polymer had a consistency K of 70 Pa·s and an index n of 0.24.

Fermentation was continued for 113 hours. 66 g/kg polymer were obtained.

Yield/saccharose consumed: 83%

EXAMPLES 4 and 5

Two fermentations were carried out in an oil/water emulsion containing 0.875 liter of the oily phase and 14.125 liters of the aqueous phase.

The composition of the fermentation medium was as follows:

(i) Saccharose: 8%

(ii) Soluble corn extract (CSL): 4%

(iii) MgSO₄.7H₂O: 0.05%

(iv) Oil: 3.5%

(v) Surfactants: 1.5%

The oily phase consisted of rapeseed oil and natural fatty ethoxyalcohols (CEMULSOL AS 5-SFOS Company) and, for Example 4, of aliphatic hydrocarbons (EXSOL D 89) and ethoxynonylphenols (50/50 mixture of CEMULSOL NP 4 and CEMULSOL NP 17) for Example 5.

Fermentation conditions were as follows:

Temperature: 28° C.

| | Aeration | Agitation |
| --- | --- | --- |
| 0–17 hours: | 0.92 VVM | 390 rpm |
| after 17 hours: | 1.39 VVM | 500 rpm |
| after 41 hours: | 1.39 VVM | 500 rpm (Ex. 4) |
| | | 600 rpm (Ex. 5) |

Fermentation was continued until all of the saccharose was consumed:

| Results: | Example 4 | Example 5 |
| --- | --- | --- |
| Duration: | 68 hours | 80 hours |
| Active material: | 47.4 g/kg | 51 g/kg |
| Yield/saccharose: | 60% | 64% |

Using 1 ml of a preculture of *Xanthomonas campestris* on a MF culture medium having 10 g/liter saccharose, 100 ml of an emulsified oil/water medium contained in a 500 ml Erlenmeyer flask were seeded.

The aqueous phase common to both examples was identical to that of Example 3.

The composition of the oily phase was varied. Each flask contained 95% by weight of the aqueous phase and 5% by weight of the oily phase. The flask was agitated using a rotating agitator, revolving at 220 rpm at an amplitude of 5 cm, and incubated at 28° C. for 89 hours.

The results are reported in Table II.

TABLE I

| Aging | Xanthomonas UFC/ml of emulsion | | Resistivity v · cm | |
|---|---|---|---|---|
| (hours) | Ex. 1 | Ex. 2 | Ex. 1 | Ex. 2 |
| 0 | $1.6 \times 10^8$ | $3.9 \times 10^7$ | 216 | — |
| 17 | $4 \times 10^8$ | $3 \times 10^9$ | 216 | — |
| 23 | $8 \times 10^9$ | $5.4 \times 10^9$ | 370 | 354 |
| 43 | $7 \times 10^8$ | $2 \times 10^{10}$ | 216 | 354 |
| 66 | $4 \times 10^8$ | $1.2 \times 10^{10}$ | 216 | 277 |
| 90 | $1 \times 10^8$ | | 185 | 262 |

TABLE II

| | Example | 6* | 7 | 8 | 9 | 10 | 11 | 12 | 13 | 14 |
|---|---|---|---|---|---|---|---|---|---|---|
| Oil** | Rapeseed | | 3.5 | 3.5 | | | | | | |
| | Soybean | | | | 3.5 | 3.5 | | | | |
| | Exsol D 80 | | | | | | 3.5 | 3.5 | | |
| | Isopar M | | | | | | | | 3.5 | 3.5 |
| Surfac- | Cemulsol NP 4 | | 1.5 | | | | 1 | 0.75 | 1 | 0.75 |
| tant** | Cemulsol NP 17 | | | | | | 0.5 | 0.75 | 0.5 | 0.75 |
| (g) | Cemulsol R 5 | | | | 1.35 | | | | | |
| | Cemulsol T | | | | 0.15 | | | | | |
| | Cemulsol NP 5 | | | | | 1.5 | | | | |
| | Cemulsol AS 5 | | | 1.5 | | | | | | |
| pH | | 6.75 | 6.2 | 6.5 | 6.55 | 6.35 | 6.3 | 5.75 | 6 | 5.9 |
| Viscosity*** (mPa · s) | | 9,600 | 11,700 | 7,400 | 8,700 | 11,100 | 7,000 | 10,500 | 12,900 | 12,900 |
| Sugar consumed (g/l) | | 45.6 | 49.5 | 60.5 | 47.2 | 48.4 | 54.5 | 63.3 | 62.2 | 67.1 |
| Polymer (g/kg) | | 32.4 | 41.3 | 33.8 | 35 | 36 | 35.9 | 41.2 | 41.2 | 42.8 |
| Yield/sugar consumed | | 71 | 83 | 89 | 74 | 74 | 66 | 65 | 66 | 64 |

*Control - no oil
**Exsol D 80 - Aliphatic hydrocarbons, Esso Chimie
Isopar M: Isoparaffins - Esso Chimie
Cemulsol NP 4, NP 5, NP 17: ethoxynonylphenols, Societe SFOS
Cemulsol R5, AS 5, T: ethoxyoleocetyl alcohols, Societe SFOS
***Brookfield, 20° C., needle No. 4, 30 t/min While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the production of polysaccharide biopolymers by fermentation of *Xanthomonas campestris*, wherein the entire fermentation process is effected by culturing *Xanthomonas campestris* in an aqueous nutrient medium which is mixed with an oil containing composition under conditions resulting in an oil-in-water emulsion comprising 1 to 18% by weight of a discontinuous oil phase.

2. The process of claim 1, wherein said oil containing composition comprises a mineral or vegetable oil.

3. The process of claim 2, wherein the oil composition comprises an oil selected from the group consisting of isoparaffins, deodorized kerosene, high boiling point hydrocarbons, rapeseed oil, soybean oil, corn oil, sunflower oil, peanut oil and mixtures thereof.

4. The process of claim 1, wherein said discontinuous oily phase comprises from about 3 to 16% by weight of the oil-in-water emulsion.

5. The process of claim 1, wherein said oil-in-water emulsion comprises a stabilizing amount of at least one nonionic surface active agent.

6. The process of claim 5, wherein said at least one nonionic surface active agent having an HLB of no more than about 11.

7. The process of claim 6, wherein said at least one nonionic surface active agent has an HLB value of from about 6 to 11.

8. The process of claim 1, further comprising concentrating said oil-in-water emulsion, after fermentation, to produce a concentrate containing from 8 to 60% by weight of the polysaccharide biopolymers.

9. The process of claim 1, wherein the pH of the aqueous nutrient medium is maintained constant during fermentation.

* * * * *